United States Patent [19]
Holley et al.

[11] Patent Number: 6,039,690
[45] Date of Patent: Mar. 21, 2000

[54] METHOD AND APPARATUS FOR FREQUENCY CONTROL OF AN ULTRASOUND SYSTEM

[75] Inventors: Gregory L. Holley, Mountain View; Paul E. Chandler, Santa Cruz, both of Calif.

[73] Assignee: Acuson Corporation, Mountain View, Calif.

[21] Appl. No.: 09/156,157

[22] Filed: Sep. 17, 1998

Related U.S. Application Data

[60] Division of application No. 08/904,829, Aug. 1, 1997, and a continuation-in-part of application No. 08/877,148, Jun. 17, 1997, abandoned.

[51] Int. Cl.[7] .................................................. A61B 8/00
[52] U.S. Cl. ............................................ 600/440; 600/450
[58] Field of Search .................................. 600/440, 441, 600/443, 447, 450, 458

[56] References Cited

U.S. PATENT DOCUMENTS

| | | |
|---|---|---|
| 3,640,271 | 2/1972 | Horton . |
| 4,712,037 | 12/1987 | Verbeek et al. . |
| 5,111,823 | 5/1992 | Cohen . |
| 5,115,809 | 5/1992 | Saitoh et al. . |
| 5,135,000 | 8/1992 | Akselrod et al. . |
| 5,158,071 | 10/1992 | Umemura et al. . |
| 5,195,520 | 3/1993 | Schlief et al. . |
| 5,197,477 | 3/1993 | Peterson et al. . |
| 5,233,994 | 8/1993 | Shmulewitz . |
| 5,255,683 | 10/1993 | Monaghan . |

(List continued on next page.)

FOREIGN PATENT DOCUMENTS

| | | |
|---|---|---|
| 0 357 164 | of 0000 | European Pat. Off. . |
| 0 770 352 A1 | 5/1997 | European Pat. Off. . |
| 0851241 A2 | 7/1998 | European Pat. Off. . |
| WO91/15999 | 10/1991 | WIPO . |

OTHER PUBLICATIONS

Declaration of Gregory L. Holley, Dated Oct. 14, 1999.

P.N. Burns, et al, Harmonic Power Mode Doppler Using Microbubble Contrast Agents: An Improved Method For Small Vessel Flow Imaging, 1994 Ultrasonics Symposium, pp. 1547–1550.

T.G. Leighton, "Transient excitation of insonated bubbles." Research Notes.

Eric J. Chen, et al., "Young's Modulus Measurements of Soft Tissues with Application to Elasticity Imaging." IEEE Transactions on Ultrasonics, Ferroelectrics, and Frequency Control, vol. 43, No. 1, Jan. 1996.

Pi Hsien Chang, et al., "Second Harmonic Imaging and Harmonic Doppler Measurements with Albunex." IEEE Transactions on Ultrasonics, Ferroelectrics, and Frequency Control, vol. 42, No. 6, Nov. 1996.

(List continued on next page.)

*Primary Examiner*—Francis J. Jaworski
*Attorney, Agent, or Firm*—Craig A. Summerfield, Esq.; Brinks Hofer Gilson & Lione

[57] ABSTRACT

A method and system for acquiring data in an ultrasound system are provided. A transducer is operatively connected to a transmit beamformer and a receive beamformer. The receive beamformer is configured to obtain a first value associated with a fundamental frequency interleaved with a second value associated with a harmonic frequency. A first transmit signal is transmitted at a first frequency. A first echo signal is received in response to the first transmit signal. At least the first value associated with the first frequency is obtained from the first echo signal. An interleaved second transmit signal is transmitted at the first frequency or a second frequency. A second echo signal is received in response to the second transmit signal. At least the second value associated with a third frequency is obtained from the second echo signal. Images are generated and displayed based on the at least one first value and the at least one second value.

12 Claims, 5 Drawing Sheets

U.S. PATENT DOCUMENTS

| | | |
|---|---|---|
| 5,287,753 | 2/1994 | Routh et al. . |
| 5,313,948 | 5/1994 | Murashita et al. . |
| 5,358,466 | 10/1994 | Aida et al. . |
| 5,386,830 | 2/1995 | Powers et al. . |
| 5,396,285 | 3/1995 | Hedberg et al. . |
| 5,409,688 | 4/1995 | Quay . |
| 5,410,205 | 4/1995 | Gururaja . |
| 5,417,213 | 5/1995 | Prince . |
| 5,417,214 | 5/1995 | Roberts et al. . |
| 5,425,366 | 6/1995 | Reinhardt et al. . |
| 5,433,204 | 7/1995 | Olson . |
| 5,433,207 | 7/1995 | Pretlow, III . |
| 5,435,311 | 7/1995 | Umemura et al. . |
| 5,438,554 | 8/1995 | Seyed-Bolorforosh et al. . |
| 5,443,071 | 8/1995 | Banjanin et al. . |
| 5,456,255 | 10/1995 | Abe et al. . |
| 5,456,257 | 10/1995 | Johnson et al. . |
| 5,469,849 | 11/1995 | Sasaki et al. . |
| 5,471,990 | 12/1995 | Thirsk . |
| 5,479,926 | 1/1996 | Ustuner et al. . |
| 5,482,046 | 1/1996 | Deitrich . |
| 5,526,816 | 6/1996 | Arditi . |
| 5,540,909 | 7/1996 | Schutt . |
| 5,555,534 | 9/1996 | Maslak et al. . |
| 5,558,092 | 9/1996 | Unger et al. . |
| 5,560,364 | 10/1996 | Porter . |
| 5,568,812 | 10/1996 | Murashita et al. . |
| 5,577,505 | 11/1996 | Brock-Fisher et al. . |
| 5,579,768 | 12/1996 | Klesenki . |
| 5,579,770 | 12/1996 | Finger . |
| 5,581,517 | 12/1996 | Gee et al. . |
| 5,588,435 | 12/1996 | Weng et al. . |
| 5,601,085 | 2/1997 | Ostensen et al. . |
| 5,601,086 | 2/1997 | Pretlow, III et al. . |
| 5,608,690 | 3/1997 | Hossack et al. . |
| 5,617,862 | 4/1997 | Cole et al. . |
| 5,623,928 | 4/1997 | Wright et al. . |
| 5,624,382 | 4/1997 | Oppelt et al. . |
| 5,628,322 | 5/1997 | Mine . |
| 5,632,277 | 5/1997 | Chapman et al. . |
| 5,675,554 | 10/1997 | Cole et al. . |
| 5,724,976 | 3/1998 | Mine et al. . |
| 5,833,613 | 11/1998 | Averkiou et al. . |
| 5,891,038 | 4/1999 | Seyed-Bolorforosh et al. ....... 600/447 |
| 5,916,168 | 6/1999 | Pedersen et al. ....................... 128/916 |

OTHER PUBLICATIONS

Marc Gensane, "Bubble population measeurements with a parametric array." 1994 Acoustical Society of America, 95 (6), Jun.

Ken Ishihara et al., "New Approach to Noninvasive Manometry Based on Pressure Dependent Resonant Shift of Elastic Microcapsules in Ultrasonics Frequency Characteristics." Japanese J. of Applied Physics, vol. 2 (1988).

Shmuel Gottlieb, M.D. et al., " Effect of Pressure on Echocardiographic Videodensity from Sonicated Albumin: An In Vitro Model." J. Ultrasound Med. 14 (1995).

J. W. Norris, "The non–linear oscillation of a radially symmetric bubble in a time periodic pressure field." Dynamics and Stability of Systems, vol. 9, No. 1 (1994).

Michael S. Longuet–Higgins, Resonance in nonlinear bubble oscillations. J. Fluid Mech. (1991) vol. 224.

Chiang C. Mei, et al., "Parametric resonance of a spherical bubble." J. Fluid Mech. (1991) vol. 229.

V.L. Newhouse, et al., "Bubble size measurements using the nonlinear mixing of two frequencies." J. Acoust. Soc. Am. 75 (5), May 1984.

Janet B. Jones–Oliviera, et al., "Transient fluid—solid interaction of submerged spherical shells revisited: Proliferation of frequencies and acoustic radiation effects." Acoustical Society of America, 96(2) Pt. 1, Aug. 1994.

Chandra M. Sehgal, PhD., et al., "Sonographic Enhancement of Renal Cortex by Contrast Media." J. Ultrasound Med, 14 (1995).

"Abstract Session IV Contrast and Ischemia." and "Poster Session A New Technologies." Journal of the American Society of Echocardiography, vol. 8, No. 3, May 1995.

Chandra M. Sehgal, PhD, et al., "Influence of Postprocessing Curves on Contrast–Echographic Imaging: Preliminary Studies." J. Ultrasound Med, 14 (1995).

Deborah J. Rubens, M.D., et al., "Sonoelasticity Imaging of Prostate Cancer: In Vitro Results." Radiology, vol. 995, No. 2, 1995.

Kotaro Sato, et al., "Numerical analysis of a gas bubble near a rigid boundary in an oscillatory pressure field." J. Acoustical Society of America, 95 (5), May 1994.

L.W. Anson et al., "Ultrasonic scattering from spherical shells including viscous and thermal effects." J. Acoustical Society of America, 93 (4), Apr. 1993.

B. Schrope, et al., "Simulated Capillary Blood Flow Measurement Using A Nonlinear Ultrasonic Contrast Agent," Ultrasonic Imaging 14 (1992).

Fred Lee, Jr., M.D., et al., "Sonoelasticity Imaging: Results in in Vitro Tissue Specimens." Radiology, vol. 181, No. 1, 1991.

Kevin J. Parker, PhD, et al., "Sonoelasticity of Organs: Shear Waves Ring a Bell." J. Ultrasound Med., 11 (1992).

William Armstrong, M.D., et al., "American Society of Echocardiography Position Paper on Contrast Echocardiography." draft 1—Jun. 6, 1994.

K.J. Parker, et al., "Tissue Response to Mechanical Vibrations for 'Sonoelasticity Imaging'." Ultrasound in Med. & Biol., vol. 16, No. 3, (1990).

Robert M. Lerner, et al., "'Sonoelasticity' Images Derived from Ultrasound Signals in Mechanically Vibrated Tissued." Ultrasound in Med. & Biol., vol. 16, No. 3, (1990).

J. Ophir, et al., "Elastography: A Quantitative Method for Imaging the Elasticity of Biological Tissues." Ultrasonics Imaging 13 (1991).

J.A. Hossack et al., "Improving transducer performance using multiple active layers." SPIE vol. 1733 (1992).

Volkmar Uhlendorf, et al., "Nonlinear Acoustical Response of Coated Microbubbles in Diagnostic Ultrasound." 1994 Ultrasonics Symposium.

John A. Hossack, et al., "Improving the Characteristics of a Transduer Using Multiple Piezoelectric Layers." IEEE Transactions on Ultrasonics, Ferroelectrics, and Frequency Control, vol. 40, No. 2, Mar. 1993.

H. Edward Karrer, et al., "A Phased Array Acoustic Imaging System for Medical Use." 1980 Ultrasonics Symposium.

"HP Ultrasound Technologies—Viability." About HP Ultrasound Imaging, WWW document, 1997.

Ted Christopher, "Finite Amplitude Distortio–Based Inhomogenous Pulse Echo Ultrasonic Imaging." IEEE Transactions on Ultrasonics, Ferroelectrics, and Frequency Control, vol. 44, No. 1, Jan. 1997.

"Supplement to Journal of the American College of Cardiology" American College of Cardiology, 45th Annual Scientific Session, Mar. 24–27, 1996 pp. 21A, 63A, 239–240A.

Yang–Sub Lee, et al., "Time–domain modeling of pulsed finite–amplitude sound beams." 1995 Acoustical Society of America, 97 (2), Feb. 1995.

Michalakis A. Averkiou, et al., "Self–demodulation of amplitude–and frequency–modulated pulses in a thermoviscous fluid." J. Acoustical Society of America, 94 (5), Nov. 1993.

Nico de Jong, "Physical properties and technical aspects of ultrasound contrast agents.".

METHOD AND APPARATUS FOR FREQUENCY CONTROL OF AN ULTRASOUND SYSTEM

This application is a division of application Ser. No. 08/904,829, filed Aug. 1, 1997, (pending).

RELATED APPLICATION

The present application is a continuation-in-part of application for a METHOD AND APPARATUS FOR FREQUENCY CONTROL OF AN ULTRASOUND SYSTEM, Ser. No. 08/877,148, filed on Jun. 17, 1997 now abandoned, the disclosure of which is hereby incorporated by reference.

FIELD OF THE INVENTION

This invention generally relates to imaging systems, such as ultrasound systems. In particular, the invention relates to a system and method for generating images using multiple frequencies of echo signals.

BACKGROUND OF THE INVENTION

Ultrasound imaging systems generate and transmit ultrasound signals. Typically, the transmitted ultrasound signal is a pulse with a center frequency within the 2 to 15 MHz range. The ultrasound signal propagates through a body, such as the chest cavity of a patient. The transmitted ultrasound signal reflects off structures within the body, such as blood cells or tissue boundaries. Some of the reflected signals, echo signals, propagate towards the transducer.

As the transmit signal propagates through and scatters within the body, additional frequency components are generated, such as at harmonics of the transmit frequency. These additional frequency components continue to propagate through and reflect off structures in the body. Echo signals having the same frequencies as the transmit signal and echo signals associated with the additional frequency components impinge on the transducer. The additional frequency components are caused by non-linear propagation and non-linear scattering or reflecting.

The echo signals are detected and processed by the ultrasound system. Conventional ultrasound systems filter or otherwise remove signals having harmonic or different frequencies than the transmit frequencies. Thus, echo signals resulting from linear propagation and reflection are detected by the ultrasound system.

The detected linear echo signals are used to create an image. For example, Doppler and B-mode image information are derived from the linear echo signals. The information is then used to generate two-dimensional or graphical displays.

As an alternative and as a discussed by Ted Christopher in "Finite Amplitude Distortion-Based Inhomogeneous Pulse Echo Ultrasonic Imaging", IEEE Trans. UFFC 44(1), pp. 125–139 (January 1997), harmonic echo signals, signals resulting from non-linear propagation and scattering, are detected. The echo signals having the same or similar frequency band as the transmit signals are filtered or otherwise removed. An image, such as a B-mode image, is generated from the detected harmonic echo signals. Typically, the signal-to-noise ratio of the echo signals at harmonic frequencies may be acceptable for B-mode imaging, yet unacceptable for Doppler imaging. Various techniques for non-linear imaging are disclosed in U.S. Pat. Nos. 5,410,516 and 5,255,683.

SUMMARY OF THE INVENTION

The invention provides a method and apparatus for obtaining and displaying various ultrasound data. Information based on both harmonic and fundamental frequencies are acquired and displayed at substantially the same time. In one aspect, a method and system for acquiring data in an ultrasound system are provided. A first transmit signal is transmitted, and a linear echo signal is acquired in response to the first transmit signal. An interleaved second transmit signal is transmitted, either at the first frequency band or a second frequency band, and a non-linear echo signal is acquired in response to the second transmit signal.

In another embodiment, a method of acquiring data in an ultrasound system is provided. Data is obtained in response to a fundamental frequency. Interleaved with the data, other data is obtained in response to a harmonic frequency.

In yet another aspect of the invention, a method of displaying ultrasound information is provided. A first image responsive to non-linear echo signals is displayed. A second image responsive to linear echo signals is displayed with the first image.

DETAILED DESCRIPTION OF PREFERRED EMBODIMENTS

Figure 1:
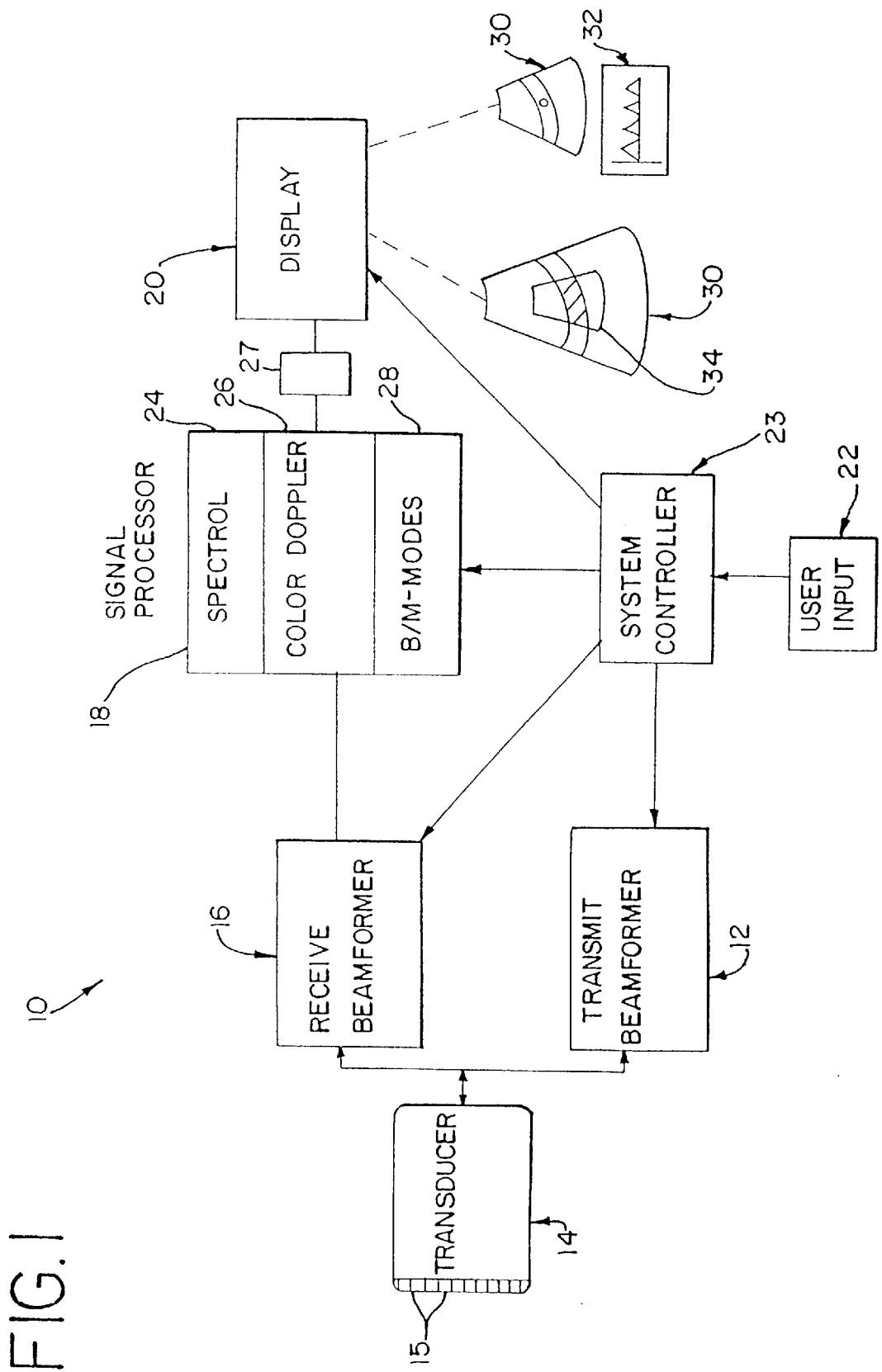
FIG. 1 is a block diagram of an ultrasound system for acquiring and imaging harmonic and fundamental frequency data.

Referring now to the figures, and in particular, FIG. 1, an ultrasound system is generally shown at 10. The ultrasound system 10 is configurable to acquire signals at one frequency band interleaved with signals at another frequency band and display information in response to the signals. For example, the ultrasound system 10 acquires data associated with a fundamental frequency band interleaved with data associated with a harmonic frequency band. Harmonic frequencies are frequencies associated with non-linear propagation or scattering of transmit signals. As used herein, harmonic includes subharmonics as well as second, third, fourth, and other harmonics. Fundamental frequencies are frequencies corresponding to linear propagation and scattering of transmit signals. Non-linear propagation or scattering corresponds to shifting energy associated with a frequency or frequencies to another frequency or frequencies. Linear propagation or scattering corresponds to energy associated with a frequency that is not shifted. Information responsive to the fundamental frequency band is displayed in some locations on a display, information responsive to the harmonic frequency band is displayed at other locations on the display.

Figure 4:
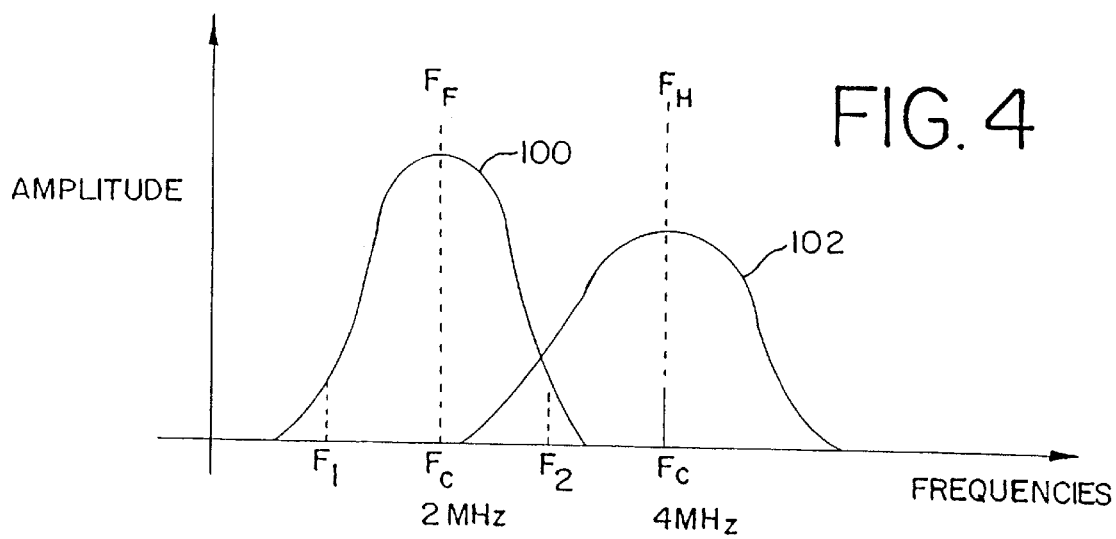
FIG. 4 is a graphical representation of received amplitudes as a function of frequency.

Referring to FIG. 4, a transmit signal with a bandwidth approximately corresponding to frequencies F1 and F2 is transmitted. A frequency band 100 represents the acquired fundamental frequencies and associated amplitudes. A frequency band 102 represents acquired frequencies and associated amplitudes corresponding to non-linear propagation or scattering. For example, the frequency band 102 corresponds to the second order harmonic frequencies of the transmitted signal. As shown in FIG. 4, some of the fundamental frequencies may also include harmonic frequency information and vice versa. More or less overlap may occur.

Referring to FIG. 1, the ultrasound system 10 includes a transmit beamformer 12, a transducer 14, a receive beamformer 16, a signal processor 18, and a display 20. The ultrasound system 10 also includes a user input 22. The user input 22 is of any construction known in the art, such as a keyboard, track ball, joy stick, touch pad, touch screen, or combination of devices. Preferably, the user input 22 is a keyboard with various dedicated keys and a track ball.

With user input 22, the user selects the type of image or images for display. The images are based on various processing modes known in the art. For example, a B-mode image, a M-mode image, a color M-mode image, a color Doppler velocity image (CDV), a color Doppler energy image (CDE), a Doppler Tissue image (DTI), a CW spectral Doppler image, or a PW spectral Doppler image may be selected. Based on the user selection of a particular mode, control signals are provided to the transmit beamformer 12 and the receive beamformer 16 to generate in phase and quadrature (I and Q) information appropriate for the particular image selected.

The user also selects the display of multiple images at the same time. For example, a B-mode image 30 and a CDV image 34 are selected. Many other combinations of images are possible, such as a B-mode image 30 and a spectral Doppler image 32 or two B-mode images 30. The combination of more than two images is also possible such as displaying a B-mode image 30, a CDV image 34, and a spectral Doppler image 32. Information associated with one image is displayed in a region, such as a point, points, ultrasound line or lines, on the display 20, and information associated with another image is displayed in another region on the display 20.

The user also selects a transmit frequency and a receive frequency associated with each image. The frequencies available for selection include at least one receive frequency that is a harmonic of the transmit frequency and at least one receive frequency that is a fundamental of the transmit frequency. Other combinations may be provided. The selected frequencies associated with each image are preferably within the frequency range of the transducer 14.

Based on input from the user input 22, a system controller 23, such as one or more microprocessors with one or more programs, provides control instructions to the transmit beamformer 12, the receive beamformer 16, the signal processor 18, and the display 20. For example, the user input 22 allows selection of transmit and receive frequencies and bands as discussed below. Programming may be used instead of user selection. The system controller 23 configures the ultrasound system 10 in accordance with the selected frequencies.

Based on the various user selections, the transmit beamformer 12 is configured. The transmit beamformer 12 is of a construction known in the art, such as a digital or analog based beamformer capable of generating signals at different frequencies. The transmit beamformer 12 generates one or more excitation signals. Each excitation signal has an associated center frequency. As used herein, the center frequency represents the frequency in a band of frequencies approximately corresponding to the center of the amplitude distribution. Referring to FIG. 4, two frequency bands 100 and 102 are shown. Since the amplitude distribution is Gaussian, the center frequency, $F_c$, is half of the sum of frequencies F1 and F2 in band 100. Other amplitude distributions with different center frequencies may be used. The center frequency associated with each excitation signal is substantially the same as the selected transmit frequency. Preferably, the center frequency of the excitation signals is within the 2 to 15 MHz range, such as 2 MHz, and accounts for the frequency response of the transducer 14. Except for CW spectral Doppler, the excitation signals preferably have non-zero bandwidth, such as represented by the bands 100 or 102.

Referring to FIGS. 1 and 4, the excitation signals from the transmit beamformer 12 are provided for the transducer 14. The transducer is of any construction known in the art, such as a multiple element 15 piezoelectric transducer. One or more of the elements 15 in the transducer 14 are excited by an excitation signal to produce ultrasonic waveforms. As known in the art, the waveforms are focused along ultrasonic beams or lines in one of various formats, such as steered linear, sector, or Vector®. The ultrasonic waves are focused using various delay and apodization techniques. The ultrasonic waves have a center frequency, such as 2 MHz, and a bandwidth associated with the frequency of the excitation signals. Thus, the center frequency of the ultrasonic waves corresponds to one of the transmit frequencies selected by the user.

The focused ultrasonic waves propagate through a body and reflect off various structures, such as blood cells and tissue, both linearly and non-linearly. Some of the reflected waves return as echo signals to the transducer 14. The echo signals excite the elements 15 of the transducer 14. The elements 15 generate voltage signals corresponding to the echo signals. These voltage signals are provided to the receive beamformer 16.

The receive beamformer 16 is of a construction known in the art, such as an analog or digital receive beamformer capable of processing signals associated with different frequencies. The receive beamformer 16 and the transmit beamformer 12 may comprise a single device. As known in the art, each voltage signal is delayed, apodized, and summed with other voltage signals. An ongoing stream of summed signals represents the ultrasound beam or line received from the body.

The receive beamformer 16 also demodulates the summed signals to baseband. The demodulation frequency is selected in response to the fundamental frequency or another frequency, such as a second order harmonic frequency. Preferably, the receive beamformer 16 is capable of demodulating in response to differing demodulocation frequencies, such as fundamental, sub-harmonic, second order harmonic, third order harmonic, or fourth order harmonic frequencies. For example, the transmitted ultrasonic waveforms are transmitted at a 2 MHz center frequency, similar to the band 100 in FIG. 4. The summed signals are then demodulated to baseband by shifting by either the fundamental 2 MHz or the second order harmonic 4 MHz frequency (the demodulation frequency). Signals associated with frequencies other than near baseband are removed by low pass filtering. As an alternative or in addition to demodulation, the receive beamformer 16 provides band pass filtering. Thus, signals associated with frequencies other than a range of frequencies centered around the desired receive minus any demodulation frequency are filtered from the summed signals. The demodulated or filtered signal is passed to the signal processor 18 as a complex I and Q signal, but other types of signals, such as real value signals, may be passed. The I and Q signals referred to herein may be replaced by other types of signals, such as the real value signals.

The signal processor 18 comprises one or more processors for generating spectral Doppler, color Doppler, B-mode, or M-mode information. Preferably, the signal processor 18 comprises a spectral Doppler processor 24, a color Doppler processor 26 and a B/M-mode processor 28. Each of these processors is preferably a digital signal processor and operates as known in the art.

The spectral Doppler processor 24 receives I and Q signals from the receive beamformer 16. The I and Q signals are generated with the transmit beamformer 12 and receive beamformer 16 using either pulse wave (PW) or continuous wave (CW) transmission techniques, as known in the art. The spectral Doppler processor 24 generates spectral information, such as frequency and associated intensity information as a function of time, as known in the art.

The color Doppler processor 26 receives the I and Q signals from the receive beamformer 16. As known in the art, the color Doppler processor 26 estimates velocity, variance of velocity and energy from the I and Q signals.

The B/M-mode processor 28 also receives I and Q signals from the receive beamformer 16. As known in the art, the B/M-mode processor 28 generates information representing the intensity of the echo signal associated with the I and Q signals.

The information generated by, the signal processor 18 is provided to a scan converter and image processor 27. The scan converter and image processor 27 is of a construction known in the art and generates the image of the type selected by the user and provides the image information to the display 20 as known in the art. The information for display is scan converted.

Scan converted information associated with one image is converted to a display value or values corresponding to a region of the display. The region is associated with a point, a plurality of points, ultrasound lines or a plurality of ultrasound lines. The information is converted to a display value with a look-up table, as known in the art. Scan converted information associated with another image is converted to a display value or values for another region of the display. Thus, display values responsive to harmonic frequencies are created for display at one or more locations, and display values responsive to fundamental frequencies are created for display at one or more locations different from the one or more locations corresponding to harmonic frequencies. For example and preferably, a larger B-mode image responsive to harmonic frequencies is selected for combined display with a smaller color Doppler image responsive to fundamental frequencies. B-mode image display values are created for regions of the image not overlapping the color Doppler image. Color Doppler image display values are created for locations where the images overlap. Thus, the B-mode and color Doppler images are displayed by region. The choice of which information is to be displayed may be made on a pixel by pixel basis, in which case the regions may be dispersed (e.g. pixels of Doppler image information dispersed within pixels of B-mode image information). Alternately, the regions of Doppler and B-mode information may include regions of contiguous pixels. If desired, the choice of which information is to be displayed for a given pixel may be made based on the values of the image information for that pixel. For example, B-mode image information may be selected for display at a given pixel unless the Doppler information for that pixel is within a selected range.

The two images may be combined as is well known in the art for a color Doppler image. As one example of a conventional image mapping, a determination may be made on a pixel-by-pixel basis whether to display scan-converted color Doppler parameters as a colored pixel or to display scan-converted B-mode intensity as a grayscale pixel. For example, the B-mode intensity may be displayed if the B-mode log intensity exceeds a threshold, such as 85% of the maximum value, or if the color Doppler energy is below a minimum threshold. Otherwise, the color Doppler parameters are converted to an [R,G,B] color value and displayed. It should be noted that in such a case, the color Doppler processor may also perform some thresholding operations, such as setting the color Doppler parameters for a point to zero if the measured velocity for that point is below some threshold. Another scheme commonly used to combine two images is simple additive blending, combined with scaling and thresholding. A B-mode pixel value (intensity, scan-converted and translated to [R,G,B] values representing a shade of gray) may be scaled and added to the [R,G,B] values representing the color parameters for a given point to produce a linear combination of the two. The total is then clipped to lie within the maximum displayable R, G, and B values. For pixels where the color parameters lie outside of certain preset ranges (for example, where the color energy is below a threshold value), the B-mode pixel value may simply be displayed unscaled. Many other variants on the above means of image combination are possible and are known in the art.

As another example, a B-mode image responsive to harmonic frequencies is selected for adjacent display with a spectral Doppler image. Other combinations of display values, such as by point, plurality of points, ultrasound line or plurality of ultrasound lines, may be used. Additionally, different processes for determining the type of display values for each location on the display 20 may be used, such as applying one or more thresholds to the information for selection between harmonic or fundamental based information. In this way, the regions of B-mode image data and the regions of Doppler image data in the combined image may be shaped in response to the image data. The conversion to display values may be performed prior to scan conversion.

As yet another alternative, information from one image may be used to modulate image information from the other image. For example, harmonic B-mode image information may be used to modulate fundamental Doppler information, as for example with a video mixer as shown in Arenson U.S. Pat. No. 5,285,788, the disclosure which is hereby incorporated by reference.

As an alternative for other applications, the scan converted information associated with different images is provided to a look-up-table. A display value representing a combination of images is output by the look-up-table. The image information represents a blended combination of images for display on the display 20. Suitable look-up table techniques are disclosed in Ustuner, U.S. Pat. No. 5,479,926.

The display 20 is a monitor or other device for displaying two-dimensional images. Preferably, the display 20 is a color monitor. The image information is displayed on the display 20. The images represent the body. For example, a B-mode image 30 is shown representing an artery. A spectral Doppler image is shown at 32, and a color Doppler image is shown at 34.

Each displayed two-dimensional image, such as a B-mode, CDV, CDE, or DTI image, is formed from multiple ultrasound lines. Each ultrasound line is formed from multiple I and Q signals or samples representing different ranges or depths along the ultrasound line. One two-dimensional image comprises a frame of ultrasound information. For spectral Doppler or M-mode, a frame of information comprises a plurality of frequencies or depths and associated intensities based on multiple samples. For color M-mode, a frame of information comprises a plurality of depths and associated velocities, energies, and/or variances of velocity based on multiple samples. Some of the multiple samples may occur in multiple frames. The multiple samples all correspond to the same location or locations within the body.

As a new frame or frames of data are obtained, a new image or images is generated for display. Alternatively, as each spectral line associated with an image is obtained, the region of the image corresponding with the new spectral line is updated or changed.

Any of the various images discussed above are generated from the I and Q signals. The I and Q signals are generated in response to either harmonic or fundamental frequencies. The frequencies used are based on the configuration of the transmit and receive beamformers 12 and 16. Thus, any of the images discussed above are either a harmonic frequency based image or a fundamental frequency based image.

To generate the combination of images discussed above, multiple images are preferably generated in an interleaved fashion, and the transmit and receive beamformers 12 and 16 are reconfigured to obtain the desired image information for each image. Each reconfiguration is based on the user selected modes and frequencies. For example, one or more ultrasound lines of information associated with the B-mode image 30 are obtained. Then, one or more ultrasound lines associated with the CDV image 34 are obtained. Alternatively, values associated with one or more points in the B-mode image are obtained. Then, values associated with one or more points in the CDV image are obtained. As yet another alternative, the interleaving process may be based on obtaining the images by frame or multiple frames. For example, a first frame of information for generating and displaying the B-mode image 30 is obtained. Subsequently, information for generating and displaying multiple frames of the CDV image 34 are obtained. Typically, the interleaving process is repeated in any of the alternatives discussed above. The displayed B-mode and CDV images 30 and 34 are continuously updated by point, ultrasound line or frame.

Figure 2:
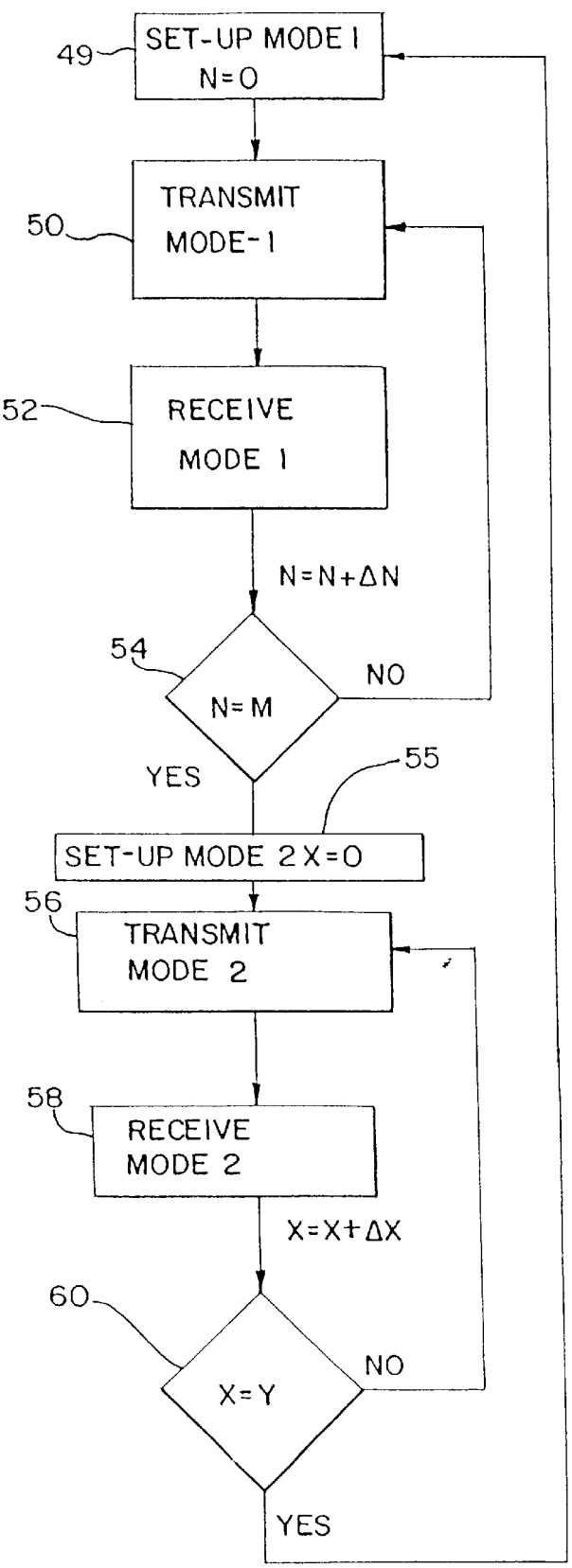
FIG. 2 is a flow diagram representing operation of an ultrasound system to acquire and image harmonic and fundamental frequency data.

Interleaving is performed as known in the art. For example, a block of B-mode lines is acquired, then varying sized blocks of B-mode and CDE lines are acquired, and finally another block of B-mode lines are acquired. The varying sizes of the blocks are selected so that B-mode and CDE information from one area in the body is acquired substantially simultaneously. Other interleaving process may be used. Referring now to FIG. 2, a flow chart demonstrating a flexible process for interleaving of an image based on fundamental frequencies and an image based on harmonic frequencies is shown. In this example, mode 1 is selected as a B-mode image received at a harmonic frequency or frequencies, and mode 2 is selected as a CDE image received at a fundamental frequency or frequencies.

The number of I and Q signals obtained with each configuration of the transmit and receive beamformers 12 and 16 is set in set-up blocks 49 and 55. The M and Y values represent the number of values obtained for a particular mode before values are obtained for another mode, such as a number of values associated with a line, group of lines, frame, or group of frames. Alternatively, M and Y represent a number of desired lines. The I and Q signals obtained in each configuration or mode represent one or more I and Q samples at the same or different depths. The desired number of mode 1 samples or lines M and the desired number of mode 2 samples or lines Y are determined as known in the art.

The M or Y values may change as any given frame of information is obtained. For example, mode 1 corresponds to a B-mode image and mode 2 corresponds to a CDV image. The CDV image is smaller and overlies the B-mode image. A group of multiple lines represent the area of the B-mode image that is to the left of the CDV image. Once the I and Q signals associated with this group of multiple lines are obtained, then the value M is reset for processing the ultrasound line information associated with the overlapping portions of the B-mode and CDV images. The M and Y values may also change while obtaining information associated with overlapping portions. Once the information associated with the overlapping portions of the two images is obtained, the values for M and/or Y are reset to obtain information associated with multiple lines of the B-mode image to the right of the CDV image. Alternatively, the number of desired mode 1 and mode 2 values, M and Y, are reset after obtaining samples representative of only a portion of an ultrasound line. As another example, the number of desired mode 1 and mode 2 values, M and Y, are selected to correspond to multiple frames of information.

To begin acquisition of samples, the system is configured for mode 1 processing in set-up block 49. The number of obtained samples N is set to zero, and the number of desired samples M is determined as discussed above. Other control parameters may be set, as known in the art.

In response to the control parameters, ultrasonic waves are transmitted in transmit mode 1 block 50. The ultrasonic waves are focused to a location or locations within the body. The ultrasonic waves are transmitted at a frequency band, such as associated with a 2 MHz center frequency. Echo signals are received in receive mode 1 block 52.

A signal or signals representing the detected echo signals are processed as discussed above. In particular, the signal or signals are demodulated or filtered to provide information associated with harmonic frequencies, such as the second order harmonic frequency (4 MHz) or a sub-harmonic. Thus, an I and Q signal or signals representing one or more locations in a body are generated by the transmit mode 1 and receive mode 1 blocks 50 and 52. The I and Q signal or signals represent non-linear propagation and scattering of the transmit signal.

The number of obtained samples, N, of I and Q signals is incremented by a value $\Delta N$ representing the number of obtained samples, such as multiple samples or lines associated with multiple beams and/or depths. In interleave block 54, N is compared to the number of desired samples or lines M. If N does not equal or exceed M, then the mode 1 process carried out by the transmit mode 1 and receive mode 1 blocks 50 and 52 is repeated. Thus, other I and Q signals associated with the same or a different location or locations in the body are obtained.

If N equals or exceeds M, then the number of obtained samples or lines, X, associated with mode 2 is set to zero in set-up block 55. The system is configured for mode 2 processing, and the number of desired samples or lines Y is selected as discussed above. X represents the number of I and Q signals or lines obtained in the mode 2 configuration. Other control parameters may be set, as known in the art.

Based on the control parameters, a focused ultrasound wave is generated and transmitted at a frequency band in transmit mode 2 block 56. For example, a focused ultrasound wave with a 2 MHz center frequency is transmitted.

Echo signals associated with the transmitted ultrasound wave are received in receive mode 2 block 58. As discussed above, a signal or signals representing the echo signals are filtered or demodulated to obtain a signal or signals associated with a frequency band, such as the fundamental 2 MHz center frequency. Thus, an I and Q signal or signals representing one or more locations in the body using the mode 2 configuration is obtained.

The number X is incremented by a value ΔX representing the number of obtained samples and compared to the number of desired mode 2 I and Q signals or lines Y in interleave block 60. If X does not equal or exceed Y, then the transmit and receive process of transmit and receive mode 2 blocks 56 and 58 is repeated.

If X equals or exceeds Y, then the desired number of mode 2 samples or lines have been obtained. N is set to zero, and the setup, transmit and receive process for mode 1 is started. Thus, the interleaved mode 1 and mode 2 processes discussed above are repeated.

Referring to FIG. 1, the mode 1 I and Q signals and mode 2 I and Q signals are provided to the signal processor 18. The signal processor 18 generates information for mode 1 and mode 2 images. For example, information associated with a B-mode image is generated based on the mode 1 I and Q signals, and information for a CDE image is generated based on the mode 2 I and Q signals. As the image information is generated, the information is provided to the scan converter and image processor 27. The image information is provided either as a single value, multiple values, multiple values associated with one or more ultrasound lines, or multiple values associated with one frame of information to the display 20.

The display 20 displays the two or more images. For example, the display 20 displays the harmonic based B-mode image with the fundamental based CDE image. Preferably, the CDE image is superimposed on the B-mode image by displaying information associated with the CDE image in one or more regions of the display and displaying information associated with the B-mode image in one or more different regions of the display. The images are interleaved due to interleaving the transmission and reception of information as discussed above. Any combination of images are interleaved and displayed, such as two B-mode or two color Doppler images, color Doppler and spectral Doppler images, B-mode and spectral Doppler images, or three or more images.

Referring to FIG. 4, the discussion above discloses reception of harmonic frequencies having a center frequency off-set from the center frequency of the transmit or fundamental frequencies. Harmonic frequencies with the same center frequency as the fundamental frequencies may also be used. Any method for distinguishing linear signals from non-linear signals may be used, such as disclosed in U.S. Pat. Nos. 5,410,516, 5,255,683, 5,577,505 and 5,632,277.

Referring to FIG. 1, the ultrasound system 10 is preferably capable of rapid configuration of the receive and transmit beamformers 12 and 16. The rapid configuring allows for interleaving between a fewer number of I and Q signals, such as interleaving values associated with a portion of an ultrasound line for one image with values associated with a portion of an ultrasound line for another image. Alternatively, the ultrasound system 10 generates values associated with one or more ultrasound lines in one image, and then generates values associated with one or more ultrasound lines in another image. As another alternative, multiple transmit and receive beamformers 12 and 16 are provided. Thus, the ultrasound system 10 interleaves without reconfiguration.

Figure 3:
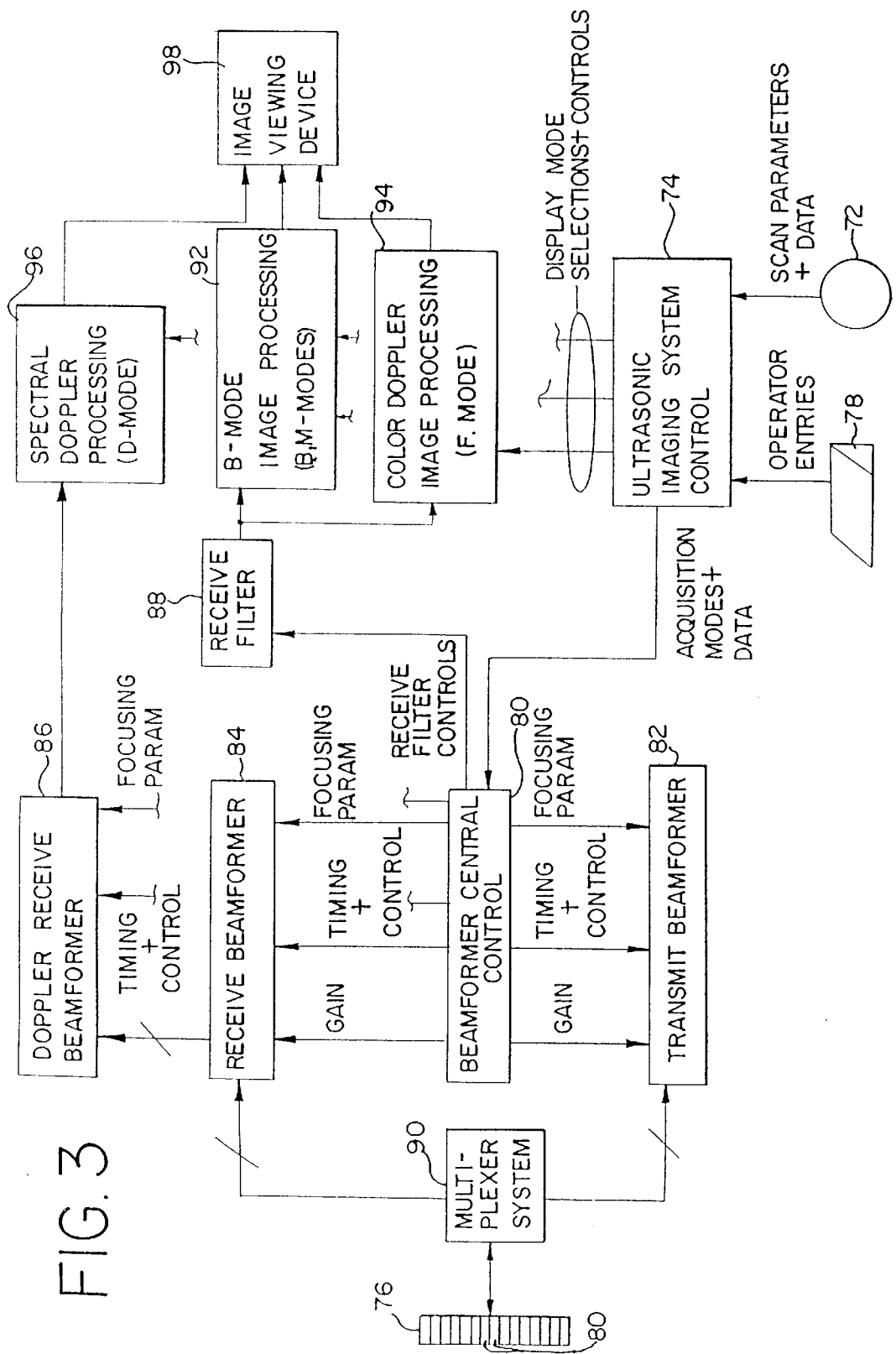
FIG. 3 is a block diagram of an alternative ultrasound system for acquiring and imaging harmonic and fundamental frequency data.

Referring now to FIG. 3, a highly programmable alternative ultrasound system is generally shown at 70. The ultrasound system 70 is disclosed in U.S. Pat. No. 5,581,517, Method And Apparatus For Focus Control Of Transmit And Receive Beamformer Systems (the '517 patent), the disclosure of which is herein incorporated by reference. The ultrasound system 70 is capable of displaying an image associated with at least one harmonic frequency interleaved and displayed with an image associated with at least one fundamental frequency. To display the images, the ultrasound system 70 generates focused ultrasonic waves based on user control and scan parameters. Echo signals are detected also based on user control and scan parameters. The detected information is processed to generate the images.

A system control 74 coordinates generation of the various images. The system control 74 is a program or programs running on one or more processors, but other control devices may be used. The system control 74 receives input information from the transducer 76 and the user input 78.

The transducer 76 is of a construction known in the art. Preferably, the transducer 76 has multiple elements 80. For example, a 19 mm 64 element transducer array is used, such as the Acuson 3V2c. Other sized and shaped transducers may be used.

The system control 74 determines the type of transducer 76 connected to the ultrasound system 70 as known in the art. Based on the type of transducer 76, the system control 74 makes various options available to the user on a display 98.

The user selects the various options with the user input 78. The user input 78 is a keyboard and track ball device, but other input devices may be used. The number or combination of images is selected, such as two or three images. The mode for each image is selected. Any of the various modes discussed above are preferably available. For example, the user selects a B-mode image and a CDV image. The user also selects the area within the body for ultrasonic scanning. Based on the type of transducer 76, the user selects a transmit and receive center frequency for each mode. Using the 3V2c transducer, the user preferably selects a single value representative of both a transmit and receive center frequency, such as either a 2, 2.5, 3, 3.5 MHz fundamental or 3.5 MHz harmonic frequency for the B-mode image. For example and preferably, the user selects a 3.5 harmonic frequency for the B-mode image (transmit centered around 1.75 MHz and receive centered around 3.5 MHz). The user also selects an available frequency for the CDV image, such as the 2 MHz fundamental frequency (transmit and receive centered around 2 MHz). More, fewer, or different fundamental or harmonic frequencies may be provided for any particular transducer.

Figure 6A:
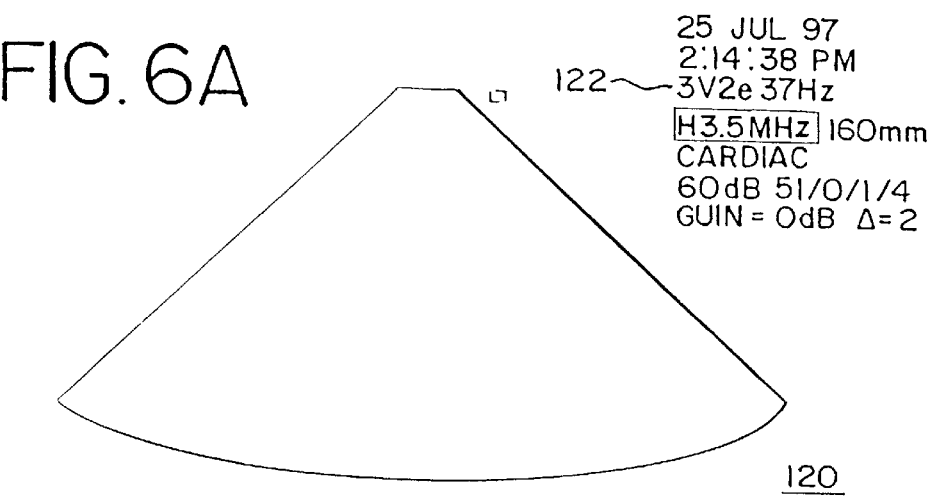
FIGS. 6A and 6B are graphical representations of screen displays.
Figure 5:
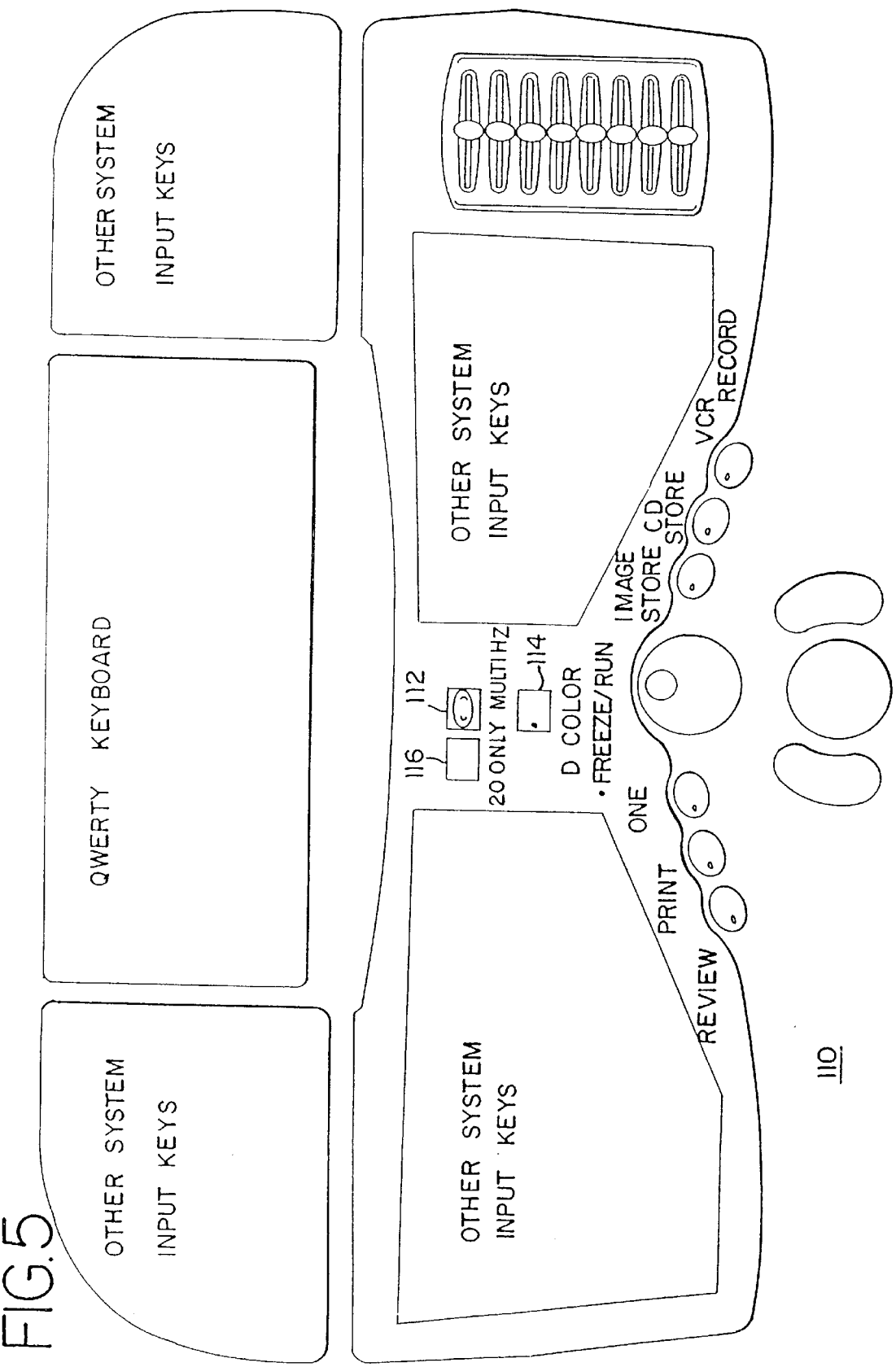
FIG. 5 is a layout diagram of a keyboard.

Referring to FIG. 5, a keyboard 110 used as part of the preferred user input 78 of FIG. 3 is shown. By connecting the transducer 76 (see FIG. 3), such as the 3V2c transducer, the system 70 (see FIG. 3) preferably defaults to a B-mode image configuration. Other defaults may be used. In order to select a combination of images, such as a B-mode image associated with a 3.5 MHz harmonic center frequency and a CDV image associated with a 2.0 MHz fundamental center frequency, the user first selects a center frequency for the default image. The user manipulates a "MultiHz" key 112 to select the center frequency. Referring to FIG. 6A, a screen display 120 indicates the selected center frequency for the user and highlights the selected image (the image associated changed based on the use of the key 112 (FIG. 5)). The field 122 demonstrates selection of the 3.5 MHz harmonic center frequency for the default B-mode image. Other screen displays may be used.

Figure 6B:
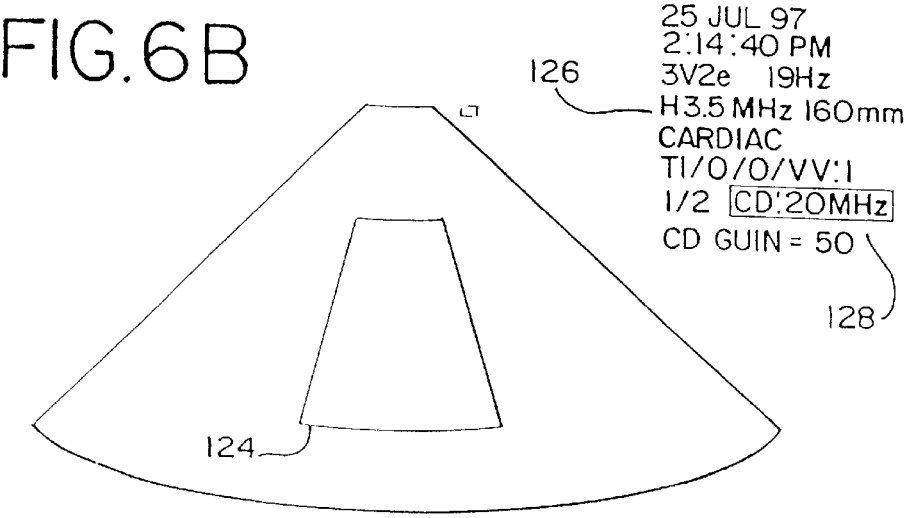

Referring to FIG. 5, the user presses the "D-color" key 114 after selecting any other parameters for the B-mode image. Pressing the key 114 preferably results in configuring the system 70 (see FIG. 3) to acquire a color Doppler image within a region of the display interleaved with the B-mode image. Referring to FIG. 6B, the region of the display associated with acquisition of color Doppler information is shown by a box 124. The type of color Doppler mode, such as CDE, CDV or DTE, is preferably selected by pressing another key.

Referring to FIG. 5, the user manipulates the "MultiHz" key 112 to select the center frequency associated with the color Doppler image, such as the 2.0 MHz fundamental center frequency. Referring to FIG. 6B, the B-mode image center frequency remains at the selected center frequency, such as the harmonic center frequency, as shown by field 126. A field 128 demonstrates selection of the 2.0 MHz fundamental center frequency for the color Doppler image. Other screen displays may be used. Preferably, the field 128 is highlighted to inform the user that manipulation of the key 112 (FIG. 5) results in changes associated with the highlighted field, such as the field 128 associated with color Doppler. Any other parameters associated with the color Doppler image are also selected by the user using other system input keys.

Referring to FIG. 5, to change the center frequency or any other parameters associated with the B-mode image, the user either presses the key 114 or a "2D only" key 116. Preferably, this causes the system 70 (FIG. 3) to remove the box 124 or the color Doppler image from the screen display. As discussed above, the key 112 may then be manipulated to select a center frequency for the B-mode image. The user returns to simultaneous or combination B-mode and color Doppler imaging by again pressing the "D color" key 114. The various color Doppler image parameters may then be further modified.

Other embodiments of the keyboard 120 of FIG. 5 or the screen display of FIGS. 6A and B are possible, such as different screen display layouts, key layouts and display of different parameters. For example, two separate keys, one for selecting the center frequency associated with each of the selected images, are provided. The center frequency associated with either image is changed without pressing another key, such as the "D color" or "2D only" keys 114 and 116. As another example, a key or group of keys are provided for selecting a harmonic center frequency while another key or group of keys, such as the "MultiHz" key 112, are used for selecting a fundamental center frequency. In another example, one key is used to select various combinations of harmonic and fundamental center frequencies for both images at the same time.

After user selection of the options discussed above and any other options available, the system control 74 obtains scan parameters. The scan parameters are stored in memory 72. Preferably, the memory 72 is a hard disk drive device, but other memories, such as RAM, tape or other disk devices, are possible. The memory 72 contains multiple data sets of scan parameters. Preferably, each data set corresponds to a transducer, a mode, selected center frequencies, a frame rate, and the selection of the size and positions of the multiple images. Other, fewer, or more variables may be used to reference a particular data set. Based on the reference variables, the system control 74 selects a certain data set or sets. In the CDV/B-mode example discussed above, two data sets are selected, each data set corresponding to one of the images. Alternatively, one data set may be selected based on the combination of images.

Each data set contains values corresponding with multiple parameters. The parameters include a nominal center frequency ($F_O$ in the '517 patent), a transmit excitation center frequency (transmit carrier frequency $F_C$ in the '517 patent), a transmit envelope, a transmit focusing frequency (see generally $V\phi$ in the '517 patent), a receive gain, an analog-to-digital (A to D) sampling rate ($F_S$ and $F_{ADC}$ in the '517 patent), a number of beams ($N_B$ in the '517 patent), a receive demodulation frequency ($F_{START}$, $\Delta F_{DOWNSLOPE}$, $F_{LIMIT}$ and $\Delta F_{UPSLOPE}$ in the '517 patent), a receive focusing frequency ($F_p(t)$ in the '517 patent), and receive filtering values. Other parameters are also stored as part of the data set, such as apodization and delay information. Different, more or fewer parameters may be used. The parameters are used as described in U.S. Pat. No. 5,581,517 and discussed below to control generation of the multiple images.

To determine values for the stored parameters, the transducer 76 is selected. The transducer frequency response is determined. For harmonic imaging, the desired transmit and receive frequencies are selected. Preferably, the receive center frequency is close to or slightly above the peak of the transducer sensitivity, and the transmit center frequency is half the receive center frequency for second order harmonic imaging. The transmit and receive center frequencies are preferably within the pass band of the transducer. Other harmonic, desired receive and desired transmit frequencies may be used. For fundamental imaging, the desired transmit and receive frequencies are selected preferably within the bandwidth of the transducer, as known in the art. Further empirical testing may provide changes in the selected values for either harmonic or fundamental imaging. Other methods and considerations for selection are possible.

The parameters discussed above are used to generate images based on harmonic frequencies or fundamental frequencies. For example, the nominal center frequency controls various system clocks and scaling parameters, such as focusing delay. The nominal center frequency is selected to be close to the desired receive center frequency. Preferably, the nominal center frequency is selected from a list of available frequencies associated with particular A to D sampling rates, as discussed below. In the preferred CDV 2 MHz fundamental frequency example, the nominal center frequency is 2 MHz. For the preferred B-mode 3.5 MHz harmonic frequency example, the nominal center frequency parameter is 3.5 MHz. Regarding the $F_O$ value in the '517 patent, the values for both the transmit and receive $F_O$ are preferably the same.

The A to D sampling rate is used to determine a rate of conversion from a received analog voltage signal to a digital signal. The A to D sample rate is selected as one of 32, 40, 48 or 56 MHz as a function of the selected nominal frequency. Other values could be used, and preferably, depend on the ultrasound system 70 capabilities. Preferably, the available nominal center frequencies are no more than one half the available A to D sampling frequencies. For example, the available nominal frequencies correspond to an available A to D sample rate divided by 4, 8 and 16. In the CDV 2 MHz fundamental frequency example, the A to D sampling rate is 32 MHz. For the B-mode 3.5 MHz harmonic frequency example, the A to D sampling rate is 56 MHz.

The transmit excitation center frequency represents the modulation frequency of the excitation signal. The transmit excitation center frequency is or is close to the desired transmit frequency. The frequency response of the transducer may be considered. In the CDV 2 MHz fundamental frequency example, the transmit excitation center frequency is 22 MHz. For the preferred B-mode 3.5 MHz harmonic frequency example, the transmit excitation center frequency is 1.75 MHz.

The transmit envelope parameter preferably comprises a number of values representing a particular envelope for each excitation signal and a sample rate for outputting the various envelope values. The transmit envelope information is selected in combination with the receive filter coefficients. For harmonic imaging, the combination is selected to provide axial resolution and fundamental rejection. The transmit envelope is preferably shaped to avoid transmitting significant energy at or near the harmonic frequency. For fundamental imaging, the combination is selected to provide optimum axial resolution and greater penetration. In the CDV 2 MHz fundamental frequency example, the transmit envelope is a 0.7 MHz bandwidth Gaussian envelope sampled at 8 MHz (see Appendix A). For the B-mode 3.5 MHz harmonic frequency example, the transmit envelope is a 1.1627 MHz bandwidth Gaussian envelope sampled at 14 MHz (see Appendix A).

The transmit focusing frequency controls some aspects of focusing the ultrasonic wave. The transmit focusing frequency is used for calculation of delay values and phasing values as known in the art. Preferably, the transmit focusing frequency is selected in harmonic imaging equal to or near the desired transmit frequency and in fundamental imaging equal to or near the receive demodulation frequency. In the CDV 2 MHz fundamental frequency example, the transmit focusing frequency is 2.19 MHz. For the B-mode 3.5 MHz harmonic frequency example, the transmit focusing frequency is 1.75 MHz.

The receive gain comprises an initial gain, various slope values, various breakpoints associated with the slope values, and a maximum value. The receive gain information is selected to avoid saturation of the receive signal and to maximize image quality. In the CDV 2 MHz fundamental frequency example, the receive gain is 43 dB for the first 30 mm of depth along a particular ultrasound line and increasing at 1.375 dB/mm after 30 mm depth to a maximum of 58.15dB. For the B-mode 3.5 MHz harmonic frequency example, the receive gain is represented as a number of breakpoints representing lines of various slope as a function of depth. Based on a 100 volt transmit voltage, the breakpoints are 24 dB at 0 mm to 24 dB at 30 mm to 37 dB at 35 mm to 56 dB at 75 mm and to 101 dB at 240 mm. The receive gain is limited to a maximum of 56.25 dB. For B-mode images, the gain values increase or decrease to compensate for transmit voltages above or below 100 volts.

The number of beams parameter represents the number of beams or ultrasound lines simultaneously produced for a given transmit and receive processing mode. The number of beams is preferably 1, 2, 3 or 4, but more beams may be used. The number of beams selected is based on the amount of space to be imaged, the frequency of the imaging, the imaging mode, the desired image frame rate, and the processing capabilities of the ultrasound system 70. In the CDV 2 MHz fundamental frequency example, the receive number of beams is 2, 3 or 4, depending on the area selected by the user and any user control of the number of beams, line decimation rate, apodization, bandwidth or other factors changing the frame rate and spatial resolution. For the B-mode 3.5 MHz harmonic frequency example, the receive number of beams is 2.

The receive demodulation frequency comprises an initial value, a downslope value, a minimum value and an upslope value. The demodulation frequency is a function of the desired receive frequency and the attenuation of ultrasound signals as a function of distance. Preferably, the receive demodulation frequency is selected equal to or near the center frequency of either the harmonic or fundamental component of the received echo signal. In the CDV 2 MHz fundamental frequency example, the receive demodulation frequency is set at 2.215 MHz minus 608 Hz/mm of depth. For the B-mode 3.5 MHz harmonic frequency example, the receive demodulation frequency is set at 4.04 MHz with a 2851 Hz decrease per mm of depth.

The receive focusing frequency comprises an initial value, a downslope value, a minimum value and an upslope value. The receive focusing frequency is used to calculate delay and phase values. Preferably, the receive focusing frequency is the same as the receive demodulation frequency.

The receive filtering values comprise filter coefficient values. The filter coefficient values control filtering to remove unwanted noise signals, unwanted image signals and signals associated with undesired harmonic or fundamental frequencies as discussed above regarding the transmit envelope. The filtering coefficients are selected based on the desired type of filter, such as a low pass or band pass filter, and the baseband frequency to be passed by the filter. Preferably, the coefficient values define a load pass filter. In the CDV 2 MHz fundamental frequency example, the receive digital filtering coefficients are shown in Appendix A. For the B-mode 3.5 MHz harmonic frequency example, the receive digital filtering coefficients are shown in Appendix A.

The parameters discussed above correspond to the ultrasound system 70 disclosed herein. Other parameter values may be used. Other systems with different parameters or parameter values may also be used.

The data set or sets of parameters selected by the system control 74 are provided to the beamformer central control 80. The beamformer central control 80 preferably comprises multiple processors for providing information to the transmit beamformer 82, the receive beamformer 84, the Doppler receive beamformer 86 and the receive filter 88. The beamformer central control 80 uses the parameters to program the transmit beamformer 82, receive beamformer 84, Doppler receive beamformer 86 and receive filter 88. By programming these various structures, the beamformer central control 80 controls interleaving of data acquisition. Thus, information associated with one image is acquired, and then information associated with a second image is acquired. For example, I and Q samples associated with multiple beams for B-mode imaging at harmonic frequencies are obtained, and then I and Q samples associated with multiple beams for the CDV image at fundamental frequencies are obtained.

To obtain samples associated with one image, the associated parameters are provided to the transmit beamformer 82. The transmit beamformer 82 comprises multiple envelope memories, apodization and phase multipliers, interpolators, delays, modulators, and encoders. Preferably, the transmit beamformer 82 comprises the transmit beamformer apparatus disclosed in Method and Apparatus for Transmit Beamformer System, U.S. patent application Ser. No. 08/673,410, filed Jul. 15, 1996, the disclosure of which is herein incorporated by reference. Other analog or digital transmit beamformers may be used. The various transmit associated parameters discussed above are provided to the transmit beamformer 82. Based on the parameters, the transmit beamformer 82 is configured to generate multiple excitation signals. The multiple excitation signals have a selected center frequency. For example, in the 2 MHz fundamental CDV image selected as discussed above, the excitation signals have a center frequency of approximately 2 MHz. In the 3.5 MHz harmonic B-mode image selected as discussed above, the excitation signals have a center frequency of approximately 1.75 MHz.

The excitation signals also have a transmit voltage level. The transmit voltage level represents the maximum voltage applied to the transducer. The transmit voltage level is determined as known in the art based on FDA limitations. For example, the transmit voltage level is calculated by software for each scanning situation as a function of parameters including the transmit envelope, the transmit frequency, the pulse repetition rate, and the location of the focus point of the ultrasonic wave.

The excitation signals are provided to a multiplexer system 90. The multiplexer system 90 includes multiplexers, demultiplexers and connectors. The multiplexer system 90 routes the excitation signals to the transducer 76. The elements 80 of the transducer 76 are excited by the excitation signals. Based on the excitation, the transducer 76 generates a focused ultrasonic wave. The center frequency associated with the ultrasonic wave is preferably approximately the same as the center frequency associated with the excitation signals. In the examples discussed above, the ultrasonic wave has a center frequency of approximately 1.75 MHz or 2 MHz.

The ultrasonic wave propagates through the body and reflects off various structures. Some of the reflection or echo signals are detected by the elements 80 of the transducer 76. In response, the elements 80 generate voltage signals, which are routed through the multiplexer system 90 to the receive beamformer 84 and receive filter 88.

The receive beamformer 84 and the receive filter 88 generate digital I and Q samples associated with the user selected receive center frequency. In the B-mode harmonic imaging example discussed above, each sample is associated with a center frequency of about 3.5 MHz (the second harmonic of the corresponding transmission signal). In the CDV fundamental imaging discussed above, each sample associated with a center frequency of about 2 MHz (the fundamental of the corresponding transmission signal).

The receive beamformer 84 comprises a receive beamformer control, multiple amplifiers, multiple decimators, multiple delay memories, multiple complex multipliers and multiple analog-to-digital converters. Preferably, the receive beamformer 84 comprises the receive beamformer disclosed in the U.S. patent application Ser. No. 08/432,615 for A Method And Apparatus For Receive Beamformer System, filed May 2, 1995, the disclosure of which is herein incorporated by reference. Other digital or analog beamformer systems may be used. The various receive parameters discussed above are provided from the beamformer central control 80. Using the parameters, receive beamformer 84 is configured to receive and process the voltage signals from the transducer 76. The voltage signals from each element 80 of the transducer 76 are delayed, apodized, focused, demodulated, and summed.

The voltage signals are demodulated to baseband. The demodulation frequency is responsive to the harmonic or fundamental frequency selected by the user. For a non-linear based image, the baseband frequency is responsive to a harmonic value of the transmission frequency. For a linear based image, the baseband frequency is responsive to a fundamental value of the transmit frequency. The demodulated voltage signals are output to the receive filter 88.

The receive beamformer 84 outputs samples at a receive sampling frequency. The receive sampling frequency is the per beam complex (I and Q pair) output sampling rate or per beam processing rate. The receive sampling frequency is a function of the number of beams and the A to D sampling rate. The receive sampling frequency is equal to the A to D sampling rate divided by the number of beams rounded up to a power of two and divided by 4. Preferably, the receive sampling frequency is automatically determined and not stored on memory 72. In the CDV 2 MHz fundamental frequency example, the receive sampling frequency is either 2 or 4 MHz per ultrasound line. The receive sampling frequency is 2 MHz if the number of beams is 3 or 4, and is 4 MHz if the number of beans is 2. For the B-mode 3.5 MHz harmonic frequency example, the receive sampling frequency is 7 MHz for each ultrasound line. The output from the receive beamformer 84 is provided to the receive filter 88.

The receive filter 88 comprises a programmable filter and sample rate converter. The receive filter 88 may be combined with the receive beamformer 84. The demodulated and summed voltage signals are provided to the filter. Based on filter coefficients provided as parameters from the beamformer central control 80, the summed signal is filtered and decimatimated or upconverted to another sample rate. Preferably, the signal is low pass filtered. The low pass filtering removes signals associated with frequencies other than at or near the baseband. Alternatively, the demodulation step is by passed or the voltage signals are not demodulated in response to the desired harmonic or fundamental frequency. The filter is programmed as a bandpass filter to remove any frequencies above or below the desired frequency band, which may correspond either to the harmonic or fundamental frequency band. The filtered signal comprises an I and Q signal.

The filtered signal is preferably phase corrected using phase correction values. The phase correction values are phase adjustments provided for each range and angle in an image for multiple ultrasound line transmission and reception. The phase correction values are calculated so that the phases of two different echo signals received along different scan lines from an assumed single point target are similar after the phase adjustment. For a pair of lines and a particular depth in the image, the phase corrections are calculated by simulating the response of the ultrasound system to linear echos scattered from the assumed point target in the vicinity of two ultrasound lines. The phase of the second line simulated response is subtracted from the phase of the first line simulated response, and the difference is subtracted from the phase of a received echo signal corresponding to the second line. A system for correcting the phase of ultrasound lines is disclosed in U.S. Pat. No. 5,623,928, the disclosure of which is herein incorporated by reference. In order to estimate the response in a harmonic mode, the calculation of the simulated response includes modeling of the transmit and receive models independently. For the 3.5 MHz harmonic example, the diffraction of a transmitted pulse is modeled as linear diffraction. The calculated response is squared to shift the center frequency to the second harmonic and to estimate the bandwidth and beam width of the second harmonic. Finally, the diffraction of the simulated harmonic pulse traveling towards the transducer is modeled as linear diffraction and propagation. For Doppler modes in general, such as the CDV 2 MHz fundamental-center frequency example, the phase correction vales are set to 0. The demodulation, filtering and phase correction steps may occur in another order.

In parallel to the receive beamformer 84 and receive filter 88, the Doppler receive beamformer 86 also processes the voltage signals from the transducer 76. In particular, the voltage signals are amplified in the receive beamformer 84. The amplified voltage signals are provided to the Doppler receive beamformer 86.

The Doppler receive beamformer 86 comprises a demodulator and range gate receiver for each voltage signal, a summer, an integrator/filter/sampler and an analog-to-digital converter. Preferably, the Doppler receive beamformer 86 is the Doppler receive beamformer disclosed in U.S. Pat. No. 5,555,534 for A Method And Apparatus For Doppler Receive Beamformer System, the disclosure of which is herein incorporated by reference. Other Doppler receive beamformers may be used, such as analog or digital Doppler receive beamformers. Additionally, the Doppler receive beamformer 86 and the receive beamformer 84 may be combined into one system. The Doppler receive beamformer 86 is configured with the receive parameters from the beamformer central control 80. Based on the parameters, the Doppler receive beamformer 86 processes the voltage signals to generate an I and Q signal. The Doppler receive beamformer 86 demodulates each voltage signal to the baseband frequency. The demodulated signals are summed and filtered. As discussed above, demodulation to the baseband frequency may be replaced with band pass filtering. The filtered, summed signal is converted from an analog signal to a digital sample. The digital sample is provided to the spectral Doppler processor 96.

Using the ultrasound system 70 discussed above, one or more samples associated with a user selected mode and frequency are obtained. Samples are continuously obtained until the desired number of samples or lines are acquired. As discussed above, the desired number of samples corresponds to a portion of an ultrasound line, an entire ultrasound line, multiple ultrasound lines, one frame, or multiple frames. For spectral Doppler, the desired number of samples is obtained to allow for the fast Fourier transform or auto regressive spectral analysis as known in the art.

Once the desired number of samples or lines are obtained, the transmit beamformer 82, the receive beamformer 84, and/or the Doppler receive beamformer 86 are reconfigured. The beamformer central control 80 provides new parameters for reconfiguration. The parameters are either stored in the beamformer central control 80 or downloaded from the memory 72. Preferably, the parameters for each imaging mode and frequency selected by the user are stored in the beamformer central control 80. As an example of reconfiguration, the transmit beamformer 82, and the receive beamformer 84 are configured with the parameters discussed above for the B-mode image (harmonic mode, 3.5 MHz receive center frequency). I and Q signals associated with the receive center frequency are obtained. After obtaining the desired number of samples, the parameters associated with the CDV image (fundamental mode, 2 MHz receive center frequency) are provided to the transmit beamformer 82 and receive beamformer 84. I and Q signals associated with the fundamental frequency are obtained. As the interleaving process discussed above continues, the beamformer central control 80 configures the transmit beamformer 82 and the receive beamformer 84.

The Doppler receive beamformer 86 is also configured in an interleaving process if a spectral Doppler image is selected for display in a combination of images. For example, the ultrasound system 70 is configured to obtain B-mode lines at harmonic or fundamental frequencies and Spectral Doppler (PW or CW) lines at fundamental or harmonic frequencies. The processing of Spectral Doppler lines is well known in the art. The Doppler receive beamformer 86 is configured to obtain information associated with harmonic or fundamental frequencies. When interleaving Spectral Doppler with B-mode, the transmit parameters are preferably updated between mode scannings. As an example, the ultrasound system 70 operates as described above for 3.5 MHz harmonic B-mode imaging, interleaved with 2.0 MHz fundamental PW spectral Doppler imaging. In this case, the following control parameters are preferably used:

Doppler nominal center frequency=2.0 MHz.

Doppler modulation frequency=2.0 MHz.

Doppler transmit focusing frequency=2.0 MHz.

Doppler transmit envelope=rectangular envelope, typically 2–127 cycles of the modulation frequency, sampled at 8.0, 4.0, or 2.0 MHz.

Other parameters and parameter values may be used. All the above frequencies are selected as a frequency within the transducer bandwidth and preferably at the lower end of that bandwidth. The length of the transmit envelope is preferably proportional to a user-selected Doppler range gate size, and the sampling frequency of the Doppler transmit envelope is selected so that the total number of samples in the envelope is less than a maximum number of samples, such as 127.

Depending on the modes selected by the user, one or more of the B-mode processor 92, color Doppler processor 94 or spectral Doppler processor 96 generates information from the I and Q signals. The B-mode processor is of a construction known in the art. Preferably, the B-mode processor includes a digital signal processor. The B-mode processor 92 generates information for a B-mode or M-mode image. For example, using signals associated with the 3.5 MHz harmonic frequency, B-mode information is generated.

The color Doppler processor 94 is of a construction known in the art. The color Doppler processor 94 preferably includes a digital signal processor for estimating Doppler velocity, variance of velocity and energy. Based on the I and Q signals and user selection a velocity, energy, or variance of velocity image, color Doppler information is generated. For example, color Doppler information for the selected CDV image discussed above is generated based on signals associated with a 2.0 MHz fundamental center frequency.

The spectral Doppler processor 96 is of a construction known in the art. Preferably, the spectral Doppler processor 96 includes a digital signal processor for performing fast Fourier transform or auto regressive analysis as known in the art. The I and Q signals, based either on continuous wave or pulse wave ultrasound transmissions, are used to generate spectral information. For example, a graph of frequency as a function of time is generated. The graph includes a range of frequencies and associated energies. The graph is preferably associated with a particular location in the body, as known in the art. The spectral information as the graph is provided to the image viewing device 98 as a spectral image.

The image viewing device 98 is a scan converter, image processor and a monitor or other viewing device, as known in the art. Preferably, the image viewing device 98 includes a color monitor. The information from the various processors 92, 94 or 96 is scan converted. The scan converted information is processed as discussed above to generate images. For example, information for the CDV image corresponding to an overlapping location with the B-mode image is used to create display values for the region of overlap. Based on the CDV information, a display value is output for the location. Thus, multiple images are generated, such as the B-mode/CDV combination image discussed above. Other processes and systems for combining images may be used. Multiple display values comprise an image or combination of images. The display values for any region of the display correspond to one of the selected images. Alternatively, display values for one or more regions correspond to blended or non-blended harmonic frequency based information and display values for one or more different regions correspond to blended or non-blended fundamental frequency based information. Blended refers to inputting multiple values associated with the same location on the display into a look-up table or other structure and outputting a single value.

The image or images are displayed on image viewing device 98. As the processors 92, 94, 96 output additional information, such as a sample, multiple samples, samples associated with an ultrasound line, samples associated with multiple ultrasound lines, samples associated with a frame, or samples associated with multiple frames, the displayed images are updated, as known in the art. Thus, images associated with harmonic frequencies and images associated with fundamental frequencies are displayed substantially simultaneously and by region. For example, the B-mode image associated with the 3.5 MHz harmonic center frequency is displayed as a gray scale image for regions of no overlap with the CDV image. The CDV image associated with the 2 MHz fundamental center frequency is combined as a color image with the B-mode image by creating display values responsive to the CDV information for the region or regions of overlap. As another example, the spectral Doppler image associated with the 2 MHz fundamental center frequency is displayed adjacent to the B-mode image. Thus, the ultrasound system 70 provides the advantages of imaging based on both harmonic and fundamental frequencies.

Referring to FIGS. 1 and 3, the ultrasound systems 10 and 70 are also capable of displaying two or more images associated with harmonic frequencies substantially simultaneously. The images associated with harmonic frequencies may or may not be displayed with an image associated with fundamental frequencies. As discussed above, the user selects the type of image, including B-mode and M-mode images, and the transmit and receive frequencies, including harmonic receive frequencies, associated with each image. For example, the user selects a B-mode image associated with a 3.5 MHz harmonic center frequency for display with a M-mode image associated with a 3.5 MHz harmonic center frequency. The center frequency associated with the M-mode image is preferably the same as or close to the center frequency selected for the B-mode image. However, the harmonic center frequency for one image may be different than the harmonic center frequency for the other image. If the B-mode image is associated with a harmonic center frequency, then the M-mode image is preferably associated with a harmonic center frequency. Other combinations, such as a fundamental center frequency based B-mode image with a harmonic center frequency based M-mode image, are possible. The images are preferably displayed adjacent to each other. To increase the frame rate, the system 70 may take advantage of the fact that some of the parameters for any two or more images are the same. Thus, the advantages of imaging based on harmonic frequencies are provided for both images. For the control parameters used in the embodiment associated with FIG. 3 for the example above, see Appendix B. Other values and other parameters may be used.

As an example of displaying more than two images, a color M-mode image is selected by the user. The user selects a two dimensional, gray scale B-mode image and an associated receive center frequency, such as a 3.5 MHz harmonic center frequency. The user also selects a color Doppler image, such as a Doppler velocity image, and an associated receive center frequency, such as a 2.0 MHz fundamental center frequency. The color M-mode image is selected based on the B-mode and Doppler velocity images and comprises two images: (1) a gray scale M-mode image of intensity as a function of time for one or more points in a subject and (2) a color scale Doppler velocity image of velocity as a function of time for the same one or more points overlaid on the gray scale M-mode image. The receive frequencies selected for the color M-mode image, such as a 3.5 MHz harmonic center frequency for the gray scale image and a 2.0 MHz fundamental center frequency for the color scale image, are preferably the same as those selected for the two-dimensional B-mode and color Doppler images, respectively. Other frequency bands may be used for each of the four images discussed above, such as three or more images associated with harmonic imaging. To increase the frame rate, the system 70 may take advantage of the fact that some of the parameters for any two or more images are the same. For the control parameters used in the embodiment associated with FIG. 3 for the example above, see Appendix C. Other values and other parameters may be used.

The color Doppler image and B-mode images are preferably displayed as discussed above (CDV information for regions of overlap). Preferably, the color M-mode image is displayed adjacent to the color Doppler and B-mode images. The color M-mode image may also be displayed without the display of the B-mode or color Doppler images. In a preferred embodiment, either the B-mode and color Doppler two-dimensional images, or the color M-mode image (comprising a gray scale M-mode image combined with a color Doppler M-mode image), but not both, are displayed in real time, while the other images are frozen on the 20 display. Thus, at any given time, the system 10 or 70 is configured to obtain data associated with either the two-dimensional images or the strip images and the other images are static on the display. The selection of the images for real time acquisition is based on user input or programming. For example, the system 10 or 70 acquires a frame of information associated with the B-mode and color Doppler images every 3 seconds or every R-wave of the cardiac cycle while continuously obtaining data associated with the color M-mode image. In an alternative embodiment, both sets of images are updated substantially simultaneously, such as interleaving between the sets of images every frame or less of data acquisition.

The ultrasound systems 10 and 70 are also capable of displaying a single image associated with harmonic frequencies. For example, the user selects display of a M-mode image associated with a 3.5 MHz harmonic center frequency without the display of any other image. For the control parameters used in the embodiment associated with FIG. 3 for the example above, see the M-mode parameters in Appendix B or C. Other values and other parameters may be used.

All of the harmonic imaging techniques described above can be used for both tissue and contrast agent harmonic imaging. In contrast agent harmonic imaging, any one of a number of well known nonlinear ultrasound contrast agents, such as micro-spheres, is added to the target or subject in order to enhance the non-linear harmonic response of the tissue or fluid. The contrast agents radiate ultrasonic energy at a harmonic of an insonifying energy at a fundamental frequency.

In tissue harmonic imaging, no additional non-linear contrast agent is added to the target, and only the native nonlinear characteristics of the tissue are relied on to create the ultrasonic image. Medical ultrasound imaging is typically conducted in a discrete imaging session for a given subject at a given time. For example, an imaging session can be limited to an ultrasound patient examination of a given tissue of interest over a period of 1/14 to 1 hour, though other durations are possible. In this case no additional nonlinear contrast agent is introduced into the tissue at any time during the imaging session. Since the harmonic imaging techniques described above can be used for both tissue and contrast agent harmonic imaging, it should be understood that the introduction of an added nonlinear contrast agent into the tissue being imaged is not implied in any of the following claims unless such added non-linear contrast agent is expressly recited.

It should be understood that many changes and modifications can be made to the embodiments described above. For example, different ultrasound systems with different levels of programmability may be used. Different transducers and system configurations may also be used. Many of the various processes discussed above may be analog or digital processes. Furthermore, the transmit frequency associated with each image may be the same or different.

It is therefore intended that the foregoing detailed description be understood as an illustration of the presently preferred embodiments of the invention, and not as a definition of the invention. It is only the following claims, including all equivalents, that are intended to define the scope of the invention.

---

APPENDIX A:

The following transmit and receive filter values represent values for the cited example. Other values may be used.
CDV 2 MHz fundamental center frequency:
Transmit Envelope = [4 7 11 19 29 44 64 88 117 148 180 210 234 250 255 250 234 210 180 148 117 88 64 44 29 19 11 7 4]
(Digital values sampled at 8.0 MHz)
Receive Filter =
[0 0 −1 −2 −3 11 55 113 141 113 55 11 −1 −2 −3 0 0]
(Digital values sampled at 4.0 MHz)
OR
[0 0 −1 2 2 −13 12 125 201 125 12 −13 2 2 −1 0] (Digital values
sampled at 2.0 MHz)
The receive filter values are for the case where the receive filter does not perform a sample rate conversion. The first set of receive filter coefficient values are for the case where the number of beams = 2. The second set of receive filter coefficient values are for the case where the number of beams = 3.
B-mode 3.5 MHz harmonic frequency:
Transmit Envelope = [4 8 14 23 36 55 79 107 140 174 205 232 249 255 249 232 205 174 140 107 79 55 36 23 14 8 4]
(Digital values sampled at 14.0 MHz)
Receive Filter = [0 0 2 8 20 39 62 80 87 80 62 39 20 8 2 0] (Digital values sampled at 7.0 MHz)
The receive filter coefficient values are for the case where the receive filter does not perform a sample rate conversion.

---

APPENDIX B:

The parameters are the same for B- and M-modes unless noted.
nominal center frequency: 3.5 MHz
A to D sample rate: 56 MHz
transmit excitation center frequency: 1.75 MHz
transmit envelope parameter:
 [4 6 9 14 20 28 39 53 70 89 111 135 160 184 207 227 242 252 255 252 242 227 207 184 160 135 111 89 70 53 39 28 20 14 9 6 4]
 (0.9 MHz Gaussian sampled at 14 MHz)
transmit focusing frequency: 1.75 MHz
receive gain breakpoints: (0 mm, 24 dB)
 (30 mm, 24 dB)
 (35 mm, 37 dB)
 (75 mm, 56 dB)
 (240 mm, 101 dB)
 * gain is for nominal 100 volts; actual gain may be increased or decreased.
 * gain is limited to 56.25 dB
number of beams: 1
receive demodulation frequency: initial value = 3.9 MHz
 downslope = 1977 Hz/mm
receive focusing frequency: same as receive demodulation freq.
receive filtering values:
 [0 5 13 21 31 42 52 59 62 59 52 42 31 21 13 5]
 (16 tap FIR filter sampled at 14.0 MHz)

---

APPENDIX C:

When the 2D B-mode and color Doppler images are active, the parameters are as disclosed in the specification and Appendix A.
When the M-mode image is active, the gray scale M-mode parameters are as disclosed in Appendix B. The color scale M-mode parameters are as follows:
nominal center frequency: 2.0 MHz
A to D sample rate: 32 MHz
transmit excitation center frequency: 2.2 MHz
transmit envelope parameter:
 [4 8 14 23 36 55 79 107 140 174 205 232 249 255 249 232 205 174 140 107 79 55 36 23 14 8 4]
 (0.7 MHz Gaussian sampled at 8 MHz)
transmit focusing frequency: 2.19 MHz
receive gain:
 43 dB for first 30 mm of depth
 increasing at 1.375 dB/mm after 30 mm to maximum of 58.15 dB
number of beams: 1
receive demodulation frequency: initial value = 2.215 MHz
 downslope = 608 Hz/mm
receive focusing frequency: same as receive demodulation freq.
receive filtering values:
 [0 0 1 4 14 34 63 89 100 89 63 34 14 4 1 0]
 (16 tap FIR filter sampled at 8.0 MHz)

---

I claim:

1. A method for acquiring data representing a subject during an imaging session with an ultrasound system, said method comprising the following acts:

(a) obtaining M-mode image data representing said subject and responsive to a harmonic receive center frequency of a fundamental transmit frequency during said imaging session, said subject being free of ultrasound contrast agent throughout the entire imaging session; and (b) displaying at least a M-mode image responsive to said M-mode data.

2. The method of claim 1 wherein (a) comprises obtaining M-mode image date responsive to a second order harmonic receive center frequency.

3. The method of claim 1 further comprising:
   (c) obtaining B-mode image data representing said subject and responsive to a B-mode receive center frequency during said imaging session; and
   (d) displaying a B-mode image responsive to said B-mode data.

4. The method of claim 3 wherein (c) comprises obtaining said B-mode image data responsive to a B-mode harmonic receive center frequency.

5. The method of claim 3 wherein (c) comprises obtaining said B-mode image data responsive to said B-mode harmonic receive center frequency that is substantially the same as said harmonic receive center frequency associated with said M-mode image data.

6. The method of claim 3 wherein (c) comprises obtaining B-mode image data responsive to a B-mode fundamental receive center frequency.

7. The method of claim 3 wherein (b) and (d) comprise displaying said M-mode image in a first region and in combination with said B-mode image.

8. The method of claim 7 wherein (b) and (d) comprise displaying said M-mode image adjacent to said B-mode image.

9. The method of claim 8 wherein (e) comprises displaying said color Doppler image responsive to a color Doppler fundamental receive center frequency and said B-mode image responsive to a B-mode harmonic receive center frequency.

10. The method of claim 7 further comprising (e) displaying a color Doppler image and a B-mode image adjacent to said color M-mode image.

11. The method of claim 3 wherein (b) and (d) comprise displaying said M-mode image in a linear combination with said B-mode image.

12. The method of claim 1 further comprising:
    (c) obtaining color Doppler image data representing said subject and responsive to a color Doppler receive center frequency during said imaging session; and
    (d) wherein the step (b) comprises displaying a color M-mode image responsive to said color Doppler image data.

* * * * *

UNITED STATES PATENT AND TRADEMARK OFFICE
CERTIFICATE OF CORRECTION

PATENT NO.   : 6,039,690
DATED        : March 21, 2000
INVENTOR(S)  : Gregory L. Holley et al.

It is certified that error appears in the above-identified patent and that said Letters Patent is hereby corrected as shown below:

Title page,
Column 1,
Line 1, under "OTHER PUBLICATIONS", change "measeurements" to -- measurements --.

Column 2,
Line 41, change "Tissued" to -- Tissues --.
Line 52, change "Transduer" to -- Transducer --.
Line 59, change "Distortio" to -- Distortion --.

Column 4,
Line 47, change "demodulocation" to -- demodulation --.

Column 5,
Line 26, delete "," (comma) immediately after "by".

Column 16,
Line 17, change "beans" to -- beams --.

Column 17,
Line 1, change "vales" to -- values --.

Column 20,
Line 41, delete "20".

Column 21,
Line 13, change "1/14" to -- 1/4 --.

UNITED STATES PATENT AND TRADEMARK OFFICE
CERTIFICATE OF CORRECTION

PATENT NO.    : 6,039,690
DATED         : March 21, 2000
INVENTOR(S)   : Gregory L. Holley et al.

It is certified that error appears in the above-identified patent and that said Letters Patent is hereby corrected as shown below:

Claim 2,
Line 2, change "date" to -- data --.

Signed and Sealed this

Eleventh Day of December, 2001

Attest:

*Attesting Officer*

NICHOLAS P. GODICI
*Acting Director of the United States Patent and Trademark Office*